(12) United States Patent
Nicolaides et al.

(10) Patent No.: US 7,060,980 B2
(45) Date of Patent: Jun. 13, 2006

(54) METHOD AND SYSTEM FOR COMBINED PHOTOTHERMAL MODULATED REFLECTANCE AND PHOTOTHERMAL IR RADIOMETRIC SYSTEM

(75) Inventors: Lena Nicolaides, Fremont, CA (US); Alex Salnik, Castro Valley, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 11/143,203

(22) Filed: Jun. 2, 2005

(65) Prior Publication Data
US 2005/0225765 A1  Oct. 13, 2005

Related U.S. Application Data

(63) Continuation of application No. 10/315,588, filed on Dec. 10, 2002, now Pat. No. 6,917,039.

(60) Provisional application No. 60/356,519, filed on Feb. 13, 2002.

(51) Int. Cl.
*G01N 21/88* (2006.01)
(52) U.S. Cl. .................. 250/358.1; 250/492.2
(58) Field of Classification Search ............. 250/358.1, 250/492.2, 495.1; 356/432
See application file for complete search history.

(56) References Cited

U.S. PATENT DOCUMENTS

| | | | |
|---|---|---|---|
| 4,579,463 A | 4/1986 | Rosencwaig et al. | 374/57 |
| 4,652,757 A * | 3/1987 | Carver | 250/360.1 |
| 4,854,710 A | 8/1989 | Opsal et al. | 356/432 |
| 5,706,094 A | 1/1998 | Maris | 356/432 |
| 5,978,074 A | 11/1999 | Opsal et al. | 356/72 |
| 6,268,916 B1 | 7/2001 | Lee et al. | 356/369 |
| 6,369,363 B1 | 4/2002 | Hauf et al. | 219/411 |
| 6,489,801 B1 | 12/2002 | Borden et al. | 324/766 |
| 6,535,285 B1 | 3/2003 | Opsal et al. | 356/369 |
| 6,661,515 B1 | 12/2003 | Worster et al. | 356/394 |
| 6,671,047 B1 | 12/2003 | Opsal et al. | 356/369 |
| 6,678,349 B1 | 1/2004 | Opsal et al. | 378/89 |
| 2002/0011852 A1 | 1/2002 | Mandelis et al. | 324/752 |

OTHER PUBLICATIONS

A. Mandelis, "Laser Infrared Photothermal Radiometry of Semiconductors: Principles and Applications to Solid State Electronics," *Solid-State Electronics*, 1998, vol. 42, No. 1, pp. 1-15.

A. Salnick et al., "Relative sensitivity of photomodulated reflectance and photothermal infrared radiometry to thermal and carrier plasma waves in semiconductors," *J. Appl. Phys.*, vol. 82, No. 4, Aug. 15, 1997, pp. 1853-1859.

(Continued)

*Primary Examiner*—Otilia Gabor
(74) *Attorney, Agent, or Firm*—Stallman & Pollock LLP

(57) ABSTRACT

A method and apparatus for evaluating a semiconductor wafer. A combination of a photothermal modulated reflectance method and system with a photothermal IR radiometry system and method is utilized to provide information which can be used to determine properties of semiconductor wafers being evaluated. The system and method can provide for utilizing a common probe source and a common intensity modulated energy source. The system and method further provide an infrared detector for monitoring changes in infrared radiation emitted from a sample, and photodetector for monitoring changes in beam reflected from the sample.

18 Claims, 1 Drawing Sheet

OTHER PUBLICATIONS

A. Rosencwaig, "Thermal Wave Characterization and Inspection of Semiconductor Materials and Devices," Chapter 5 (pp. 97-135) of *Photoacoustic and Thermal Wave Phenomena in Semiconductors*, North-Holland, New York, 1987.

* cited by examiner

METHOD AND SYSTEM FOR COMBINED PHOTOTHERMAL MODULATED REFLECTANCE AND PHOTOTHERMAL IR RADIOMETRIC SYSTEM

PRIORITY

The application is a continuation of U.S. application Ser. No. 10/315,588, filed Dec. 10, 2002 now U.S. Pat. No. 6,917,039, and which claims the benefit of U.S. Provisional Application Ser. No. 60/356,519, filed Feb. 13, 2002, which is incorporated herein by reference.

TECHNICAL FIELD

The subject invention relates to a new and improved method and apparatus for evaluating surface and subsurface features in a semiconductor. The system and method utilize and incorporate analyses of changes in the reflectivity of a sample to evaluate characteristics of the sample. The system and method also utilize and incorporate analysis of infrared radiation emitted by the sample to evaluate characteristics of the sample.

BACKGROUND OF THE INVENTION

Photothermal modulated reflectance (PMR) technique, being a physical basis for the ion-implant monitoring systems, is a well-known characterization methodology used for a variety of industrial and research applications. See for example, U.S. Pat. Nos. 4,579,463; 4,854,710 and 5,978,074, each of these references are hereby incorporated in their entirety herein by reference.

Photothermal IR radiometry (PTR) is a new emerging technology that has a number of potential advantages over existing methodologies in the characterization of electronic properties of semiconductors. In the PTR system and method, the optically induced emission of blackbody radiation (infrared radiation) at the surface of a semiconductor is measured by a remote IR sensitive detector. See e.g., "Laser Infrared Photothermal Radiometry of Semiconductors; Principles and Applications to Solid State Electronics" Mandelis, *Solid State Electronics*, Volume 42, No. 1, page 1, 1998; the entirety of this reference is hereby incorporated herein by reference; U.S. patent application Ser. No. 2002/0011852, publication date Jan. 31, 2002 (NON-CONTACT PHOTOTHERMAL RADIOMETRIC METROLOGIES AND INSTRUMENTATION FOR CHARACTERIZATION OF SEMICONDUCTOR WAFERS, DEVICES AND NON ELECTRONIC MATERIALS) (this reference is hereby incorporated herein by reference).

Investigations have been performed comparing these two techniques. For example, it has been shown that the PTR signal is extremely sensitive to the carrier plasma wave effects in semiconductors and possesses up to five orders of magnitude higher plasma-to-thermal contrast than that of the PMR method. See, "Relative Sensitivity of Photomodulated Reflectance and Photothermal Infrared Radiometry to Thermal and Carrier Plasma Waves in Semiconductors," Salnik, et al., *Journal of Applied Physics*, Volume 82 (4) page 1853, Aug. 15, 1997; the entirety of this reference is incorporated herein by reference. Given the different characteristics of PTR measurement and PMR measurements, there can be instances where it would be desirable to make both PTR and PMR measurements on a wafer sample. In the past to make both PTR and PMR measurements on a semiconductor wafer, two different measurement devices were needed. Thus, it was necessary to move the wafer sample from one measurement device to another measurement device in order to make both PTR and PMR measurements on the wafer, which resulted in not measuring at the same sample location with high accuracy. Further, the fact that PMR measurement apparatus and the PTR measurement apparatus are separate results in additional space requirement and additional expense. What is needed is a measurement apparatus, which combines both a PTR measurement system and a PMR measurement system.

SUMMARY

An embodiment of the invention is an apparatus for evaluating characteristics of a semiconductor sample. The apparatus includes a probe source, which emits a probe beam of radiation that is incident upon the sample, and reflected off the sample. The apparatus also includes a source which supplies intensity modulated energy to the sample, wherein in response to the intensity modulated energy a reflectivity of the sample changes, and wherein in response to the intensity modulated energy infrared radiation emitted by the sample changes. A photodetector is provided which detects changes in the reflected probe beam, where changes in the reflected probe beam result from the variations in the reflectivity of the sample. In this embodiment a processor system is coupled to the photodetector for analyzing changes in the reflected probe beam to evaluate characteristics of the sample. Further, an infrared detector detects the changes in the infrared radiation emitted from the sample. The processor system is also coupled to the infrared detector, wherein the processor system analyzes the changes in the infrared radiation to evaluate characteristics of the sample.

Another embodiment of the invention provides a method for evaluating characteristics of a sample. The method includes generating intensity modulated energy from source. The intensity modulated energy is directed to the surface of the sample, wherein the intensity modulated energy causes changes in infrared radiation emitted from the sample, and changes in a reflectivity of the sample. A probe beam is also directed from a probe source such that it is incident upon the sample, and reflected off the sample. The changes in the probe beam resulting from the changes in the reflectivity of the sample are monitored, and these changes are analyzed to evaluate the sample. The changes in the infrared radiation emitted from the sample are monitored and these changes are analyzed to evaluate the sample.

DETAILED DESCRIPTION

Figure 1:
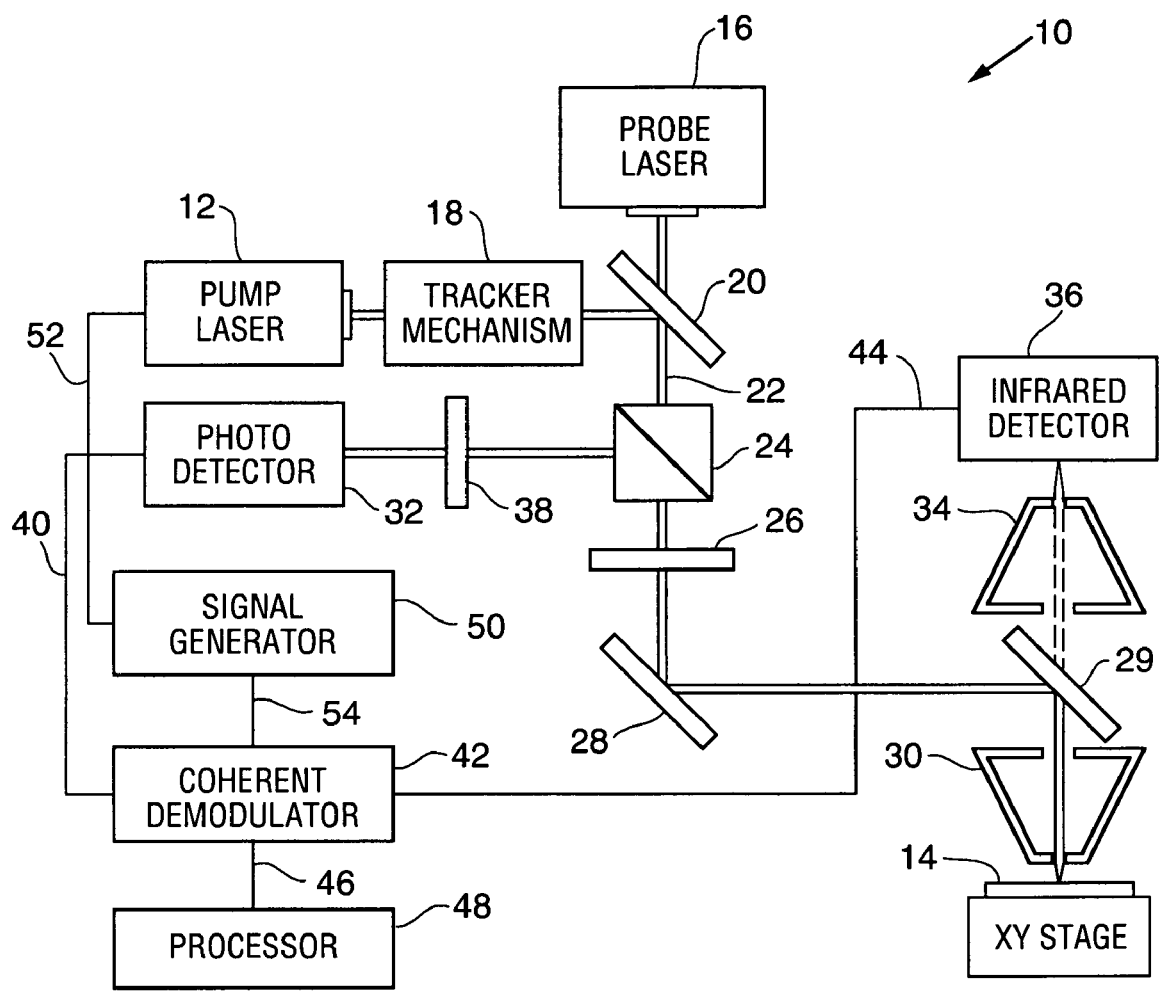
FIG. 1 is a diagram showing an embodiment of a system combining PTR and PMR measurement capability.

Due to the fact that both the PMR and PTR methods are based on the absorption of an intensity-modulated pump excitation beam, a system implementing both of these methods can share the same pump light source and the same illumination path. Thus, a combined PMR/PTR system can be obtained by modifying an existing PMR system. Besides providing PMR data, and a valuable set of independent data (PTR amplitude and phase or In-Phase and Quadrature components), in the case of a semiconductor sample, a combined PMR/PTR system can provide much higher sensitivity to the implantation dose, especially in a low dose region, and can have other application-specific advantages as compared with a standard PMR or PTR system.

An embodiment of a combined PMR/PTR system 10 is shown in FIG. 1. A first energy source 12, which can be 790 nm pump diode laser, operates as an intensity modulated energy source, where the modulation frequency can be selected, and the intensity modulated energy is focused onto the sample 14. A second energy source 16, which can be a probe diode laser at 670 nm, is also focused onto the sample and its reflection from the sample is used to detect the sample's AC response. The focused spots from the two energy sources 12 and 16 are precisely overlapped onto the sample 14 by use of a tracker 18. By precisely overlapping the beams from the two energy sources a maximum PMR signal can be achieved. The tracker 18 is used to align the intensity modulated energy from the pump laser 12 on the dichroic mirror 20. The mirror 20 reflects the intensity modulated energy from the pump laser 12 and transmits the beam from the probe laser 16, as a combined beam 22. The tracker 18 aligns the intensity modulated beam with the probe beam on the dichroic mirror 20 to produce the overlapping beams on the sample. The combined beam 22 is then transmitted through polarizing beam splitter 24. After the combined beam is transmitted through the polarizing beam splitter 24 it passes through a ¼ waveplate 26, and is then reflected off a mirror 28. The combined beam 22 is then reflected off a window 29 to a reflecting objective 30.

The window 29 can be a Germanium window, which operates as a dichroic mirror such that energy in one frequency range is transmitted through the window 29 and energy at another frequency range is reflected by the window 29. In one embodiment the window 29 is a Ge window which operates to transmit radiation at 900 nm and above, but radiation below 900 nm is reflected off the window 29.

The reflecting objective 30 is used to focus the combined beam on a diffraction limit spot on the sample of ~1 µm. The reflecting objective 30 can provide tight focusing of the combined beam on the sample 14. Further the reflecting objective 30 can also provide for efficiently collecting infrared blackbody radiation, which is emitted from the diffraction spot on the sample in response to the combined beam.

A portion of the combined beam is reflected off the sample 14. The reflected combined beam is then reflected off the window 29 and then reflected off the mirror 28, and then transmitted through the ¼ waveplate 26 a second time, which rotates the polarization of the reflected combined beam by 90 degrees. After the reflected combined beam has passed through the ¼ waveplate 26 it is incident upon the polarizing beam splitter 24 where it directed onto the photodetector 32.

In response to the combined beam incident upon the sample 14, the sample 14 emits blackbody radiation (IR radiation). This blackbody radiation is collected by the reflecting objective 30 and is transmitted through the window 29 and it is then focused by a second reflecting objective 34 onto an infrared detector 36. In one embodiment the infrared detector 36 has its peak sensitivity in the 2–12 micron wavelength range.

In one embodiment of a combined system a filter 38 is provided in front of the photodetector 32. The filter 38 operates to block the intensity modulated energy from the combined beam which is reflected from the sample, but transmits the probe beam of the combined beam to the photodetector 32. Additionally, the filter 38 can operate to block stray light so that it does not reach the photodetector. Optionally, a filter could also be included in from of the infrared detector 36.

In response to receiving the combined beam which is reflected off the sample 14, the photodector 32 generates signals 40. These signals 40 generated by the photodetector 32 are transmitted to the coherent demodulator 42. The signals 40 are pre-amplified and demodulated by the coherent demodulator 42. As shown in FIG. 1, the infrared detector generates signals 44 which are transmitted to the coherent demodulator 42. The coherent demodulator 42 operates to pre-amplify and demodulate the signal 44 output by the infrared detector 36 in response to blackbody radiation output by the sample 14. As shown, the system 10 has a single coherent demodulator 42, but it should be recognized that the system could be implemented with a separate coherent demodulator for the signals 40 output by the photodetector 32, and a separate coherent demodulator 42 for the signals 44 output by the infrared detector 36.

Signals 46 are output by the coherent demodulator 42 which correspond to the signals generated by either the photodetector 32 or the infrared detector 36. The signals 46 are processed and analyzed as PTR and PMR signals depending on the mode of operation (modes of operation discussed in more detail below). As shown in FIG. 1, the signals 46 are analyzed and processed by the processor system 48. The processor system 48 operates to determine properties of a sample based on the signals 46 which correspond to the signals generated by the photodetector 32 and the infrared detector 36. This information regarding the properties of a sample wafer can then be outputted to a user. This output could be done, for example, via a monitor, or a printer, coupled to the processor.

The analysis of the signals 46 can be done in manner similar to the analysis used in conjunction with prior systems, but instead of providing only PTR or PMR data, the processor 48 operates to utilize both reflectivity and infrared radiation information generated by the photodetector 32 and the infrared detector 36. In one embodiment the processor system 48 operates to compare changes in the reflected probe beam with measured, or modeled, changes of probe beam associated with known reference samples. By comparing the measured reflectivity data of the sample 14 with the reflectivity data for samples having known characteristics, the properties of the sample 14 being measured can be determined. Similarly, monitored changes in the infrared radiation emitted from the sample 14 can be compared with infrared radiation data for samples with known characteristics. By comparing the measured infrared radiation emitted from the sample 14 with the data for known samples, properties of the sample 14 can be determined. In one embodiment, the reflectivity data and the infrared data for the samples having known characteristics is stored in a memory device (not shown) which is coupled to the processor.

In one embodiment the system 10 will operate in two different modes. In a first mode the signal generator 50 will send a signal 52 to the pump laser 12 causing the pump laser to operate at a modulated frequency in a PMR operation range. In one embodiment, the PMR operation range can extend from approximately 0.1 kHz to well into the megahertz range (typically up to about 100 MHz). When the pump laser 12 is operating in the PMR operation range the system 10 will operate to generate PMR measurements and data. During the PMR operation the combined beam reflected off the sample 12 will be detected by the photodetector 32, and the signals 40 generated by the photodetector 32 will demodulated by coherent demodulator 42. During the demodulation of the signals 40, the coherent demodulator 42 receives a signal 54 from the signal generator 50, which corresponds to the pump laser 12 being operated in the PMR operation range, and uses this signal in conjunction with demodulating the signals 40. The signals 46 output by the coherent demodulator 42 are then analyzed to determine changes in the reflectivity of the sample 14. This reflectivity data is then used to determine other properties of the sample.

In a second mode of operation the system 10 will operate to generate infrared radiation information. In the second mode of operation the modulation frequency of the pump laser will be in a PTR operation range. Due to infrared detector limitations, the PTR operation range is typically be in the 1 kHz–1 MHz range, depending on the speed and sensitivity of the infrared detector. Higher frequencies are possible but the PTR signal in this case would be dominated by noise. While in the PTR mode the signal generator 50 generates a signal 52 which causes the pump laser 12 to operate in the PTR operation range. In this mode the signal generator 50 also operates to output a signal 54 to the coherent demodulator 42 which corresponds to the pump laser 12 operating in the PTR operation range. In some application the system 10 can operate such that the modulation frequency for the intensity modulated energy is the same for the both the PTR mode of operation and the PMR mode of operation.

The pump laser 12 could be implemented in a number of different ways. For example the pump laser 12 could be a diode laser and the modulation frequency of diode lasers can be varied electronically by the signal 52 from the signal generator 50. However, it may also be desirable to utilize a solid state laser for the pump laser 12 and to modulate its intensity using an acousto-optic modulator.

The combination of detecting systems described herein is desirable because it provides two complementary measurements (i.e. the PMR measurement and the PTR measurement). It should be understood that additional information can be also derived by combining PTR measurements with one or more other optical metrology measurements systems, including spectroscopy, spectroscopic ellipsometry, beam profile reflectometry, beam profile ellipsometry and X-ray reflection measurements. Such technologies and combinations thereof are described in U.S. Pat. No. 6,297,880 and WO 01/69215, both incorporated herein by reference.

The two independent measurements (PTR and PMR) can be used in a variety of ways to aid in the analysis of the sample. Some aspects of this analysis are discussed in examples below. It should be understood that these are only examples and that those skilled in the art could make use of the PTR and PMR measurements in a variety of different ways.

In one example, the two independent measurements could be used to improve the accuracy of the analysis of a single variable, such as ion implantation dose in the ion-implanted semiconductor sample. It is known that the PMR approach is very accurate for low and mid dose levels. However, the PMR signal becomes non-monotonic at higher doses. The availability of a second independent measurement (PTR) would allow ambiguities arising from the PMR measurement to be reduced. Such an approach could be implemented in a conventional fashion, where a series of reference wafers are fabricated with various dose levels. Each of the wafers is then measured with both techniques. The actual dose levels are then measured with a different technology (such as a four point probe). Calibration curves are developed for both sets of measurements. When subsequent test measurements of a sample are made, the results can be compared to the calibration curves to determine the best solution for dose.

The most basic approach for combining the two measurements is to average the two results for dosage. The averaging could be weighted based on the dose region or other factors. Another possibility would be to use the PTR signal to select the appropriate cycle in the PMR response and use the PMR response to define the dose.

The multiple independent measurements could be used in more sophisticated analyses. PMR measurements made at multiple different modulation frequencies, spots sizes and/or power levels can be used to analyze the sample as a function of depth. These measurements can be fit to a model to determine variations in composition, damage, etc. In this invention, an expanded model including one or more PTR measurements could be derived. The data from both types of measurements can be combined in iterative regressive analysis to determine sample parameters.

In another example, a combination of the PMR and PTR measurements could be used to improve the accuracy of the analysis of ultrashallow junctions (i.e. junctions formed by implantation with ultra low energies followed by the activation of dopants) both prior to and after annealing. The high sensitivity of the PTR measurements to photoinduced plasma can provide additional information about the implantation dose, junction depth, and electronic parameters of the doped region, such as the carrier mobility. For this purpose, both the PTR and PMR measurement modes could be used separately as well as in combination.

In yet another example, a combined PMR and PTR system could be used for characterization of metal layers on semiconductors. Both the PTR and PMR measurements are sensitive to the thickness and composition of metal layers and the combination of the two measurements could provide accurate data regarding the thickness, thermal and structural properties of metal layers. A proper calibration procedure could establish a correlation between the PTR and PMR signal characteristics (amplitude and phase) and the parameters of interest.

While the method and apparatus of the present invention has been described in terms of its presently preferred and alternate embodiments, those skilled in the art will recognize that the present invention may be practiced with modification and alteration within the spirit and scope of the appended claims. The specifications and drawings are, accordingly, to be regarded in an illustrative rather than a restrictive sense. Further, even though only certain embodiments have been described in detail, those having ordinary skill in the art will certainly understand that many modifications are possible without departing from the teachings thereof. All such modifications are intended to be encompassed within the claims set forth below.

We claim:

1. An apparatus for evaluating characteristics of a sample comprising:

an intensity modulated pump laser beam;

optics for focusing the pump laser beam onto the surface of the sample to periodically excite the sample;

a probe laser beam directed to reflect off the periodically excited sample;

a photodetector for monitoring the modulated changes in the reflected probe beam resulting from the periodic excitation of the sample and generating first output signals;

an infrared detector for monitoring modulated changes in the infrared radiation emitted from the sample resulting from the periodic excitation of the sample and generating second output signals; and a processor for receiving the first and second output signals and for using a combination of said first and second output signals to evaluate the sample.

2. An apparatus as recited in claim 1, wherein modulation frequency of the pump laser beam is selected to be higher during the generation of the first output signals used by the processor to evaluate the sample than during the generation of the second output signals used by the processor to evaluate the sample.

3. A method of evaluating the characteristics of a sample comprising:

periodically exciting the surface of the sample;

monitoring the modulated changes in reflectivity at the surface of the sample resulting from the periodic excitation of the sample and generating first output signals;

monitoring the modulated changes in the infrared radiation emitted from the sample resulting from the periodic excitation of the sample and generating second output signals; and evaluating the sample based on the combination of the first and second output signals.

4. A method as recited in claim 3, wherein the frequency at which the sample is excited is higher during the generation of the first output signals than during the generation of the second output signals that are used to evaluate the sample.

5. A method as recited in claim 3, wherein the sample is evaluated by averaging the information derived from the first and second output signals.

6. A method as recited in claim 3, wherein the sample is evaluated by combining the information derived from the first and second output signals with an iterative regression analysis.

7. A method as recited in claim 3, wherein the first and second output signals are used to evaluate the ion implant dosage level in the sample.

8. A method as recited in claim 3, wherein the first and second output signals are used to evaluate the junction depth of an ultrashallow junction in the sample.

9. A method as recited in claim 3, wherein the first and second output signals are used to evaluate characteristics of a metal layer on the sample surface.

10. An apparatus for evaluating characteristics of a sample comprising:

an intensity modulated pump laser beam;

optics for focusing the pump laser beam onto the surface of the sample to periodically excite the sample in a manner to cause the sample to emit modulated radiation;

a probe laser beam directed to reflect off the periodically excited sample;

a photodetector for monitoring the modulated changes in reflected probe beam resulting from the periodic excitation of the sample and generating first output signals;

a radiation detector for monitoring the modulated radiation emitted from the sample and generating second output signals; and a processor for receiving the first and second output signals and for using a combination of said first and second output signals to evaluate the sample.

11. An apparatus as recited in claim 10, wherein the modulation frequency of the pump laser beam is selected to be higher during the generation of the first output signals used by the processor to evaluate the sample than during the generation of the second output signals used by the processor to evaluate the sample.

12. A method of evaluating the characteristics of a sample comprising:

periodically exciting the surface of the sample;

monitoring the modulated changes in reflectivity at the surface of the sample resulting from the periodic excitation of the sample and generating first output signals;

monitoring the modulated changes in radiation emitted from the sample resulting from the periodic excitation of the sample and generating second output signals; and evaluating the sample based on the combination of the first and second output signals.

13. A method as recited in claim 12, wherein the frequency at which the sample is excited is higher during the generation of the first output signals than during the generation of the second output signals that are used to evaluate the sample.

14. A method as recited in claim 12, wherein the sample is evaluated by averaging the information derived from the first and second output signals.

15. A method as recited in claim 12, wherein the sample is evaluated by combining the information derived from the first and second output signals with an iterative regression analysis.

16. A method as recited in claim 12, wherein the first and second output signals are used to evaluate the ion implant dosage level in the sample.

17. A method as recited in claim 12, wherein the first and second output signals are used to evaluate the junction depth of an ultrashallow junction in the sample.

18. A method as recited in claim 12, wherein the first and second output signals are used to evaluate characteristics of a metal layer on the sample surface.

* * * * *